United States Patent
Imwinkelried et al.

(10) Patent No.: US 10,478,529 B2
(45) Date of Patent: *Nov. 19, 2019

(54) MAGNESIUM ALLOY WITH ADJUSTABLE DEGRADATION RATE

(71) Applicant: DEPUY SYNTHES PRODUCTS, INC., Raynham, MA (US)

(72) Inventors: Thomas Imwinkelried, Oberdorf (CH); Stefan Beck, Oberdorf (CH); Peter Uggowitzer, Ottenbach (CH); Joerg Loeffler, Greifensee (CH)

(73) Assignee: DePuy Synthes Products, Inc., Raynham, MA (US)

(*) Notice: Subject to any disclaimer, the term of this patent is extended or adjusted under 35 U.S.C. 154(b) by 669 days.

This patent is subject to a terminal disclaimer.

(21) Appl. No.: 14/774,264

(22) PCT Filed: Mar. 11, 2014

(86) PCT No.: PCT/US2014/023047
§ 371 (c)(1),
(2) Date: Sep. 10, 2015

(87) PCT Pub. No.: WO2014/159328
PCT Pub. Date: Oct. 2, 2014

(65) Prior Publication Data
US 2016/0022876 A1    Jan. 28, 2016

Related U.S. Application Data

(60) Provisional application No. 61/783,554, filed on Mar. 14, 2013, provisional application No. 61/909,100, (Continued)

(51) Int. Cl.
C22F 1/06    (2006.01)
A61L 31/02   (2006.01)
(Continued)

(52) U.S. Cl.
CPC ............ *A61L 31/022* (2013.01); *A61B 17/84* (2013.01); *A61F 2/44* (2013.01); *A61F 2/82* (2013.01);
(Continued)

(58) Field of Classification Search
None
See application file for complete search history.

(56) References Cited

U.S. PATENT DOCUMENTS

| | | | |
|---|---|---|---|
| 3,320,055 | A | 5/1967 | Foerster |
| 9,593,397 | B2 | 3/2017 | Imwinkelried et al. |

(Continued)

FOREIGN PATENT DOCUMENTS

| | | |
|---|---|---|
| CN | 1743486 | 3/2006 |
| CN | 1792383 A | 6/2006 |

(Continued)

OTHER PUBLICATIONS

Zhang, Mechanical Properties, degradation performance and cytotoxicity of—Mg—Zn—Ca biomedical alloys with different compositions, Materials Science and Engineering, vol. C31, 2011, 1667-1673.

(Continued)

*Primary Examiner* — Jie Yang
(74) *Attorney, Agent, or Firm* — BakerHostetler

(57) ABSTRACT

An alloy and an implant having a three-dimensional structure based on such alloy. The alloy comprises a MgZnCa alloy containing nanosized precipitates being less noble than the Mg matrix alloy and having a Zn content ranging 0.1 wt. % Zn to 2 wt. % Zn and a calcium content ranging from 0.2 wt. % to 0.5 wt. %, and having one or more other elements, with the remainder being Mg. Any second phase generated during the solidification process may be completely dissolved by a solution heat treatment. Finely dispersed nano- (Continued)

sized precipitates can then be generated by a subsequent aging heat treatment step. These precipitates are used to "pin" the grain boundaries and to prevent the coarsening of the grain structure during further processing to achieve grain sizes below 5 µm.

10 Claims, 8 Drawing Sheets

Related U.S. Application Data filed on Nov. 26, 2013, provisional application No. 61/942,951, filed on Feb. 21, 2014.

(51) Int. Cl.

| | |
|---|---|
| C22C 23/04 | (2006.01) |
| A61L 27/04 | (2006.01) |
| A61L 27/58 | (2006.01) |
| A61L 31/14 | (2006.01) |
| A61B 17/84 | (2006.01) |
| A61F 2/44 | (2006.01) |
| A61F 2/82 | (2013.01) |

(52) U.S. Cl.
CPC ............ *A61L 27/047* (2013.01); *A61L 27/58* (2013.01); *A61L 31/148* (2013.01); *C22C 23/04* (2013.01); *C22F 1/06* (2013.01)

(56) References Cited

U.S. PATENT DOCUMENTS

| | | |
|---|---|---|
| 2008/0031765 A1 | 2/2008 | Bodo et al. |
| 2010/0075162 A1 | 3/2010 | Yang et al. |
| 2011/0054629 A1 | 3/2011 | Seok et al. |
| 2011/0192500 A1 | 8/2011 | Uggowitzer et al. |
| 2012/0035740 A1 | 2/2012 | Kim |
| 2012/0095548 A1 | 4/2012 | Gregorich |
| 2012/0269673 A1 | 10/2012 | Kim |
| 2013/0131814 A1 | 5/2013 | Kim |
| 2013/0144290 A1 | 6/2013 | Schiffl |
| 2013/0209195 A1 | 8/2013 | Kuwabara et al. |
| 2014/0065009 A1 | 3/2014 | Imwinkelried |
| 2014/0261911 A1 | 9/2014 | Imwinkelried et al. |
| 2015/0129091 A1 | 5/2015 | Mueller |
| 2015/0129092 A1 | 5/2015 | Mueller |
| 2016/0022876 A1 | 1/2016 | Imwinkelried et al. |

FOREIGN PATENT DOCUMENTS

| | | |
|---|---|---|
| CN | 1792384 | 6/2006 |
| CN | 101629260 | 1/2010 |
| CN | 101658691 | 3/2010 |
| CN | 101899600 | 12/2010 |
| DE | 1483204 A1 | 10/1969 |
| EP | 1959025 | 8/2008 |
| EP | 2864515 A1 | 4/2015 |
| EP | 2971206 A1 | 1/2016 |
| JP | 2010-275634 A | 12/2010 |
| WO | WO 2004/013364 | 2/2004 |
| WO | WO 2009/147861 A1 | 12/2009 |
| WO | WO 2012/003522 | 1/2012 |
| WO | 2012/049990 | 4/2012 |
| WO | WO 2013/107644 | 7/2013 |
| WO | 2014/001241 A1 | 1/2014 |
| WO | WO 2014/001321 | 1/2014 |
| WO | 2014/159328 A1 | 10/2014 |

OTHER PUBLICATIONS

Sugiura et al., A Comparative Evaluation of Osteosynthesis With Lag Screws, Miniplates, or Kirschner Wires for Mandibular Condylar Process Fractures, Journal of Oral Maxillofac Surg, 2001.

Farahany, et al., In-situ thermal analysis and macroscopical characterization of Mg—xCa and Mg—0.5Ca—xZn alloy systems, Thermochimica Acta 2012, 180-189.

Bamberger, Trends in the Development of New Mg Alloys, Annu. Rev. Mater. Res, 2008.

Zhang et al., "Research on an Mg—Zn Alloy as a Degradable Biomaterial", Acta Materialia, Jun. 10, 2010, No. 6, 626-640.

Zhang et al., "Enhanced Mechanical Properties in Fine-Grained Mg-1,ozn-0.5Ca Alloys Prepared by Extrusion at Different Temperatures", Scripta Materialia, Nov. 1, 2010, vol. 63, No. 10, 1024-1027.

Oh-Ishi et al., "Age-Hardening Response of Mg-0.3at.%Ca Alloys With Different Zn Contents", Materials Science and Engineering, Nov. 25, 2009, vol. 526, No. 1-2, 177-184.

Oh et al., "TEM and 3DAP Characterization of an Age-Hardened Mg—Ca—Zn Alloy", Scripta Materialia, Sep. 1, 2005, vol. 53, No. 6, 675-679.

Somekawa et al., "High Strength and Fracture Toughness Balance on the Extruded Mg—Ca—Zn Alloy", Materials and Engineering, Apr. 20, 2007, vol. 459, No. 1-2, 366-370.

Oh-Ishi et a., "Influence of Zn Additions on Age-Hardening Response and Microstructure of Mg-0.3at% Ca Alloys", Magnesium Technology 2010, Proceedings of a Symposium Held During TMS Annual Meeting & Exhibition, Jan. 1, 2010, 517-520.

Li et al., "Microstructure, Mechanical Properties and Corrosion Behavior of Mg—1Zn—0.5Ca Alloy", Advanced Materials Research, Jan. 1, 2011, vol. 311-313,1735-1740.

Yang et al., "Comparison of As-Cast Microstructures and Solidification Behaviours of Mg—Zn—A1 Ternary Magnesium Alloys With Different Zn/Al Mass Ratios", Advanced Materials Research, Jan. 1, 2012, vol. 548, 322-324.

Witte et al., "Degradable Biomaterials Based on Magnesium Corrosion", Curr. Opin. Solid State Mater., Sci, Aug. 2008, 12, 63-72.

Staiger et al., "Magnesium and its Alloys as Orthopedic Biomaterials: A Review", Biomaterials, Oct. 2006, 27, 1728-1734.

Zberg et al., "MgZnCa Glasses Without Clinically Observable Hydrogen Evolution for Biodegradable Implants", Nat. Mater., Nov. 2009, 8, 887-891.

Hanzi et al., "Design Considerations for Achieving Simultaneously High-Strength and Highly Ductile Magnesium Alloys", Philos, Mag. Lett., Sep. 2012, 92, 417-427.

Tapiero et al., "Trace Elements in Human Physiology and Pathology: Zinc and Metallothioneins", Biomed. Pharmacother., Mar. 2003, 57, 399-411.

Stefanidou et al., "Zinc: A Multipurpose Trace Element", Arch. Toxicol., Sep. 2006, 80, 1-9.

Gunde et al., "High-Strength Magnesium Alloys for Degradable Implant Applications", Mater. Sci. Eng. A, Sep. 2011, 528, 1047-1054.

Hanzi et al., "Design Strategy for Microalloyed Ultra-Ductile Magnesium Alloys", Philos. Mag. Lett., Jun. 2009, 89, 377-390.

Koike, "Dislocation Plasticity and Complementary Deformation Mechanisms in Polycrystalline Mg Alloys", Mater. Sci. Forum, Mar. 2004, 449-452, 665-668.

Koike et al., "The Activity of Non-Basil Slip Systems and Dynamic Recovery at Room Temperature in Fine-Grained AZ31B Magnesium", Acta Mater., Apr. 2003, 51, 2055-2065.

Mendis et al., "Precipitation-Hardenable Mg—2.4Zn—0.1Ag—0.1Ca—0.16Zr (at.%) Wrought Magnesium Alloy", Acta Mater., Feb. 2009, 57, 749-760.

Homma et al., "Effect of Zr addition on the Mechanical Properties of As-Extruded Mg—Zn—Ca—Zr Alloys", Mater. Sci. Eng. A, Apr. 2010, 527, 2356-2362.

Kraus et al., "Magnesium Alloys for Temporary Implants in Osteosynthesis: In Vivo Studies of Their Degradation and Interaction With Bone", Acta Biomater., Mar. 2012, 8, 1230-1238.

Pichler et al., "Immunological Response to Biodegradable Magnesium Implants", JOM, Feb. 5, 2014, 1-7.

Liu et al., "Calculated Phase Diagrams and the Corrosion of Die-Cast Mg—Al Alloys", Sci., Mar. 2009, 51, 602-619.

Bakhsheshi-Rad et al., "Relationship between the corrosion behavior and the thermal characteristics and microstructure of Mg—0.5Ca—xZn alloys," Corros, Sci., Jul. 2012, 64, 184-197.

(56) References Cited

OTHER PUBLICATIONS

Hanawalt et al., "Corrosion Studies of Magnesium and Its Alloys," Trans. AIME, Feb. 1942, vol. 147, 273-299.
Hillis et al., Paper presented at SDCE 14th International Die Casting Congress and Exposition, Toronto, Canada, Paper No. G-T87-003, May 1987, 1-7.
Song et al., "Corrosion Mechanisms of Magnesium Alloys", Adv. Eng. Mater., Sep. 1999, 1, 1, 11-33.
Song et al., "Understanding Magnesium Corrosion", Adv. Eng. Mater., Dec. 2003, 5, 12, 837-858.
Song et al., Paper presented at the Magnesium Technology Conference at TMS, New Orleans, LA, Feb. 2001, 255-262.
Schinhammer et al., "On the Immersion Testing of Degradable Implant Materials in Simulated Body Fluid: Active pH Regulation using CO2", Adv. Eng. Mater., Jun. 2013, 15, 6, 434-41.
Cao et al., "Corrosion of Ultra-High-Purity Mg in 3.5% NaCl Solution Saturated With Mg(OH)2", Corros. Sci., Jun. 2013, 75, 78-99.
Kalb et al., "Impact of Microgalvanic Corrosion on the Degradation Morphology of WE43 and Pure Magnesium Under Exposure to Simulated Body Fluid", Corros. Sci., Jan. 2012, 57, 122-130.
Hanzi et al., "On the In Vitro and In vivo Degradation Performance and Biological Response of New Biodegradable Mg—Y—Zn Alloys", Acta Biomater., May 2010, 6, 1824-1833.
Yamamoto et al., "Effect of Inorganic Salts, Amino Acids and Proteins on the Degradation of Pure Magnesium in Vitro", Mater. Sci. Eng. C, 2009, 29, Jun. 1559-1568.
Kirkland et al., "Assessing the Corrosion of Biodegradable Magnesium Implants: A Critical Review of Current Methodologies and their Limitations", Acta Biomater., Mar. 2012, 8, 925-936.
Kirkland et al., "Buffer-Regulated Biocorrosion of Pure Magnesium", J. Mater. Sci. Mater. Med., Feb. 2012, 23, 283-291.
Abidin et al., "Corrosion of High Purity Mg, Mg2Zn0.2Mn, ZE41 and AZ91 in Hank's Solution at 37° C.", Corros. Sci., Jul. 2011, 53, 3542-3556.
Abidin et al., "The In Vivo and In Vitro Corrosion of High-Purity Magnesium and Magnesium Alloys WZ21 and AZ91", Corros. Sci., Jun. 2013, 75, 354-366.
Song et al., "The Role of Second Phases in the Corrosion Behavior of Mg—5Zn Alloy", Corros. Sci.,Apr. 2012, 60, 238-245.
Cha et al., "Biodegradability Engineering of Biodegradable Mg Alloys: Tailoring the Electrochemical Properties and Microstructure of Constituent Phases", Scietif. Rep., Aug. 2013, 3, 1-6.
Bakhsheshi-Rad et al., "Characterization and Corrosion Behavior of Biodegradable Mg—Ca and Mg—Ca—Zn Implant Alloys", Appl. Mech. Mater., Jan. 2012, 121-126, 568-572.
Zhang et al., "Microstructure, Mechanical Properties and Bio-Corrosion Properties of Mg—Zn—Mn—Ca Alloy for Biomedical Application", Mater. Sci. Eng. A, Jun. 2008, 497, 111-118.
Du et al., "Effects of Zn on the Microstructure, Mechanical Property and Bio-Corrosion Property of Mg—3Ca Alloys for Biomedical Application", Mater. Chem. Phys., Feb. 2011, 125, 568-575.
Kirkland et al., "In-Vitro Dissolution of Magnesium-Calcium Binary Alloys: Clarifying the Unique Role of Calcium Additions in Bioresorbable Magnesium Implant Alloys", J. Biomed. Mater. Res. B Appl. Biomater., Oct. 2010, 95, 91-100.
Wilson et al., "Effects of Preferred Orientation on the Grain Size Dependence of Yield Strength in Metals", Philos. Mag., Jun. 1963, 8, 1543-1551.
Barnett et al., "Influence of Grain Size on the Compressive Deformation of Wrought Mg—3A1—1Zn", Acta Mater., Aug. 2004, 52, 5093-5103.
Gottstein et al., Grain Boundary Migration in Metals: Thermodynamics, Kinetics, Applications, Boca Raton FL, CRC Press, Taylor & Francis Group, 2010, 1-685.
Sudholz et al., "Electrochemical Properties of Intermetallic Phases and Common Impurity Elements in Magnesium Alloys", Electrochem, Solid-State Lett., Jun. 2011, 14(2), C5-C7.
Manohar et al., "Five Decades of the Zener equation", ISIJ Int., Mar. 1998, 38, 9, 913-924.
L'Ecuyer et al., "Precipitation Interactions With Dynamic Recrystallization of a HSLS Steel", Acta Metall., Apr. 1989, 37, 4, 1023-1031.
Li, et al., "Preparation and in vitro degradation of the composite coating with high adhesion strength on biodegradable Mg Zn Ca alloy," Materials Characterization, Elsevier, New York, NY, US, vol. 62, No. 12, Jul. 10, 2011, 1158-1165.
Wang et al., "Biocorrosion of coated Mg Zn Ca alloy under constant compressive stress close to that of human tibia," Materials Letters, North Holland Publishing Company, Amsterdam, NL., vol. 70, Dec. 2, 2012, 174-176.
International Search Report for International application PCT/US2013/057294 dated Jan. 31, 2014; 6 pages.
International Search Report for International application PCT/US2014/023047 dated Jun. 17, 2014; 16 pages.
Birbilis et al. "A Combined Neural Network and Mechanistic Approach for the Prediction of Corrosion Rate and Yield Strength of Magnesium-Rare Earth Alloys", Corrosion Science, 53 pp. 168-176, Jan. 2011.
Birbilis et al. "On the Corrosion on Binary Magnesium-Rare Earth Alloys", Corrosion Science, 51, pp. 683-689, Mar. 2009.
Chia et al. "The Effect of Alloy Composition on the Microstructure and Tensile Properties of Binary Mg-rare Earth Alloys" Intermetallics, 17, pp. 481-490, Jul. 2009.
Sudholz et al., "Corrosion Behaviour of Mg-alloy AZ91E With Atypical Alloying Additions", Journal of Alloys and Compounds, 471, pp. 109-115, Mar. 2009.
Mendis et al., "An Enhanced Age Hardening Response in Mg_Sn Based Alloys Containing Zn", Materials Science & Engineering, 435-436, pp. 163-171, Nov. 2006.
Hofstetter et al., "High-Strength Low-Alloy (HSLA) Mg—Zn—Ca Alloys with Excellent Biodegradation Performance" The Minerals, Metals & Materials Society, JOM, vol. 66, No. 4, pp. 566-572, Feb. 2014.
Shaw, "Corrosion Resistance of Magnesium Alloys", ASM Handbook, vol. 13A Corrosion: Fundamentals, Testing, and Protection, pp. 692-696, 2003.
Song, Control of Biodegradation of Biocompatable Magnesium Alloys, Corrosion Science 49, pp. 1696-1701, Feb. 2007.
Yu Sun et al., Preparation and characterization of a new biomedical Mg—Zn—Ca alloy, Materials and Design, vol. 34, pp. 58-64, Feb. 2012.

MAGNESIUM ALLOY WITH ADJUSTABLE DEGRADATION RATE

CROSS REFERENCE TO RELATED APPLICATIONS

This application is a National Stage Application filed under 35 U.S.C. 371 of International Application No. PCT/US2014/023047, filed Mar. 11, 2014, which claims priority to U.S. Provisional Application No. 61/783,554, filed Mar. 14, 2013; U.S. Provisional Application No. 61/909,100, filed Nov. 26, 2013; and U.S. Provisional Application No. 61/942,951, filed Feb. 21, 2014; the disclosures of which are hereby incorporated by reference in their entireties.

BACKGROUND OF THE INVENTION

Magnesium implants were clinically used for the treatment of bone fractures by several surgeons back in the 1930s. For instance, J. Verbrugge (1934) used both pure magnesium and Mg-8% Al alloy implants on 21 patients. However, after the Second World War, the use of magnesium as a resorbable implant material fell into oblivion. In recent years, researchers have renewed their interest in resorbable magnesium implants. A main focus of magnesium research is the development of alloys and coatings. The major goals are to control the degradation rate, to avoid the formation of gas bubbles during degradation and to avoid potentially harmful alloying elements. Therefore, a need exists for magnesium alloys with a homogenous degradation behavior whose rate of degradation can be controlled and/or tuned as desired.

Commercial grade pure magnesium (3N—Mg) has poor mechanical properties in comparison with alloys like AZ91 or WE43. The possibilities to harden pure magnesium are quite limited. Hardening might be achieved by refining the grain microstructure using plastic deformation to induce dynamic recrystallization (e.g. by extrusion). The fine grained microstructure is not only necessary to achieve a better strength level but also needed to avoid mechanical anisotropy (strength difference between tension and compression). The microstructure might not be stable, though.

Embodiments of the present invention overcome one or more of above-noted challenges.

BRIEF SUMMARY OF THE INVENTION

The present disclosure provides several exemplary embodiments of the present invention, some of which are discussed below.

In an aspect, the present invention provides an MgZnCa alloy composition and an implant having a three-dimensional structure based on such alloy composition.

In one embodiment, the alloy composition comprises a Mg matrix; and, optionally, nanosized precipitates; wherein the composition has a Zn content ranging from 0.1 wt. % Zn to 2.0 wt. % Zn; a Ca content ranging from 0.2 wt. % Ca to 0.5 wt. % Ca; a content of one or more other elements; and a remainder content being Mg; wherein the nanosized precipitates are less noble or more noble than the Mg matrix, or a mixture thereof. In another embodiment, the MgZnCa alloy composition consists essentially of a Mg matrix; and, optionally, nanosized precipitates; wherein the composition has a Zn content ranging from 0.1 wt. % Zn to 2.0 wt. % Zn; a Ca content ranging from 0.2 wt. % Ca to 0.5 wt. % Ca; a content of one or more other elements; and a remainder content being Mg; wherein the nanosized precipitates are less noble or more noble than the Mg matrix, or a mixture thereof. In another embodiment, the MgZnCa alloy composition consists of a Mg matrix; and, optionally, nanosized precipitates; wherein the composition has a Zn content ranging from 0.1 wt. % Zn to 2.0 wt. % Zn; a Ca content ranging from 0.2 wt. % Ca to 0.5 wt. % Ca; a content of one or more other elements; and a remainder content being Mg; wherein the nanosized precipitates are less noble or more noble than the Mg matrix, or a mixture thereof.

In some such embodiments, the alloy composition is substantially free of microgalvanic elements. In other such embodiments, the alloy composition is monophasic. In other such embodiments, the total of other elements is less than about 0.1 wt % of the composition. In other such embodiments the one or more other elements are located in a secondary phase. In other such embodiments, the nanosized precipitates are less noble than the Mg matrix and comprise $(Mg,Zn)_2Ca$. In other such embodiments, the nanosized precipitates are more noble than the Mg matrix and comprise $Mg_6Zn_3Ca_2$. In some such embodiments, the alloy comprises nanosized precipitates that are less noble than the Mg matrix and nanozized precipitates that are more noble than the Mg matrix.

In some embodiments of the alloy according to the present invention, the alloy has a grain size of: less than 10 µm; less than 5 µm; or less than 2 µm. In some embodiments of the alloys of present invention, the alloy has a yield strength of at least 180 MPa. In one embodiment, the alloy has an ultimate tensile strength of at least 240 MPa. In another embodiment, the alloy has at least 10% elongation at break. In yet another embodiment, the alloy has an in vitro degradation rate of less than 0.5 $mg/cm^2$/day as measured in a simulated body fluid.

In other embodiments, the implant is an orthopedic implant. In such embodiments, the orthopedic implant comprises one or more of the following: a nail, a screw, a staple, a plate, a rod, a tack, a bolt, a bolt to lock a intramedullary ("IM") nail, an anchor, a dowel, a plug, a peg, a sleeve, a mesh, a transconnector, a nut, a shaped body, spinal cage, a wire, a K-wire, a woven structure, clamp, splint, scaffold, foam and honeycomb structure. In some other embodiments, the implant has a lower degradation rate compared to magnesium alloy implants containing microgalvanic impurities.

In other embodiments, the implant is a non-orthopedic implant. In such embodiments, the non-orthopedic includes a cardiovascular stent, a neuro stent and a vertebroplasty stent.

In yet another embodiment of the implant, each alloy has an in vitro degradation rate of less than 0.5 $mg/cm^2$/day as measured in a simulated body fluid.

In an aspect, the present invention provides a method of producing an alloy according to the embodiments described herein. In one embodiment, the method comprises: (a) casting an alloy containing (i) commercially pure magnesium having a purity of at least 99.96 wt. %; and (ii) from 0.1 to 2.0 wt. % zinc having a purity of at least 99.9 wt. % and (iii) from 0.2 to 0.5 wt % calcium having a purity of a least 99.9 wt %, said casting preferably being performed in an inert atmosphere and an inert reaction vessel; (b) solution heat treating the cast alloy at two different temperatures wherein a first temperature is below an eutectic temperature of Mg—Zn and a second temperature is above the eutectic temperature of the ternary Mg—Zn—Ca system to thereby form a MgZnCa alloy containing from 0.1 wt. % Zn to 2 wt. % Zn and 0.2 wt % Ca to 0.5 wt % Ca (c) aging heat treatment between 100° C. and 300° C.; and (d) extruding the alloy into a desired shape.

The impurity limits for the magnesium are preferably: Fe<30 ppm, Cu<20 ppm, Ni<5 ppm, Mn<200 ppm, Si<200 ppm whereas the total amount of these impurities should preferably be below 400 ppm.

BRIEF DESCRIPTION OF THE DRAWINGS

FIG. 4, comprising

FIGS. 6A-6B, is a bar graph depicting mean hydrogen evolution during immersion in TRIS buffered simulated body fluid for certain Mg alloys that were subjected to certain heat treatments.

DETAILED DESCRIPTION OF THE INVENTION

Figure 1:
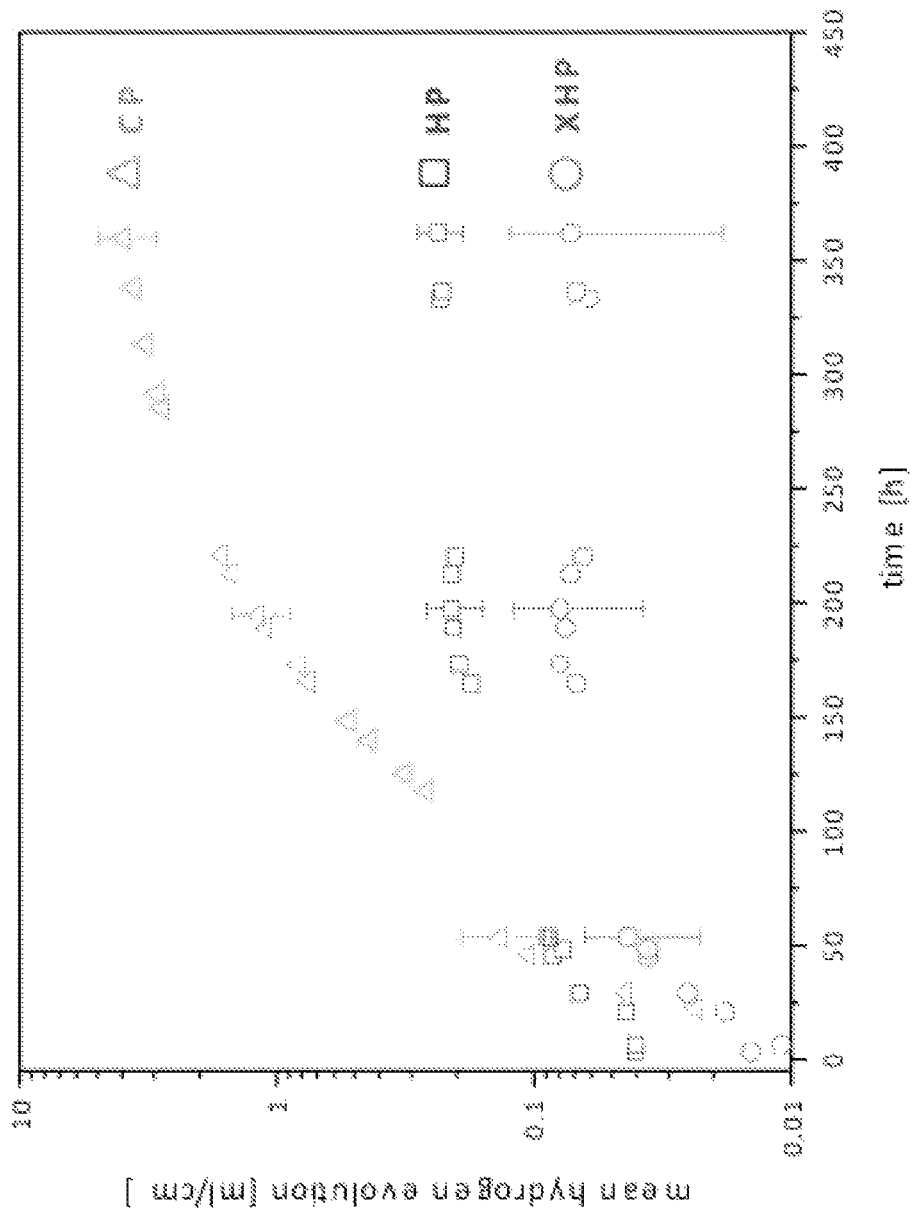
FIG. 1 is a graphical representation of mean hydrogen evolution versus time of certain Mg alloys.

Reference will now be made in detail to the various embodiments of the present disclosure. In one embodiment, the MgZnCa alloy composition comprises a Mg matrix; and, optionally, nanosized precipitates; wherein the composition has a Zn content ranging from 0.1 wt. % Zn to 2.0 wt. % Zn; a Ca content ranging from 0.2 wt. % Ca to 0.5 wt. % Ca; a content of one or more other elements; and a remainder content being Mg; wherein the nanosized precipitates are less noble or more noble than the Mg matrix, or a mixture thereof. In another embodiment, the MgZnCa alloy composition consists essentially of a Mg matrix; and, optionally, nanosized precipitates; wherein the composition has a Zn content ranging from 0.1 wt. % Zn to 2.0 wt. % Zn; a Ca content ranging from 0.2 wt. % Ca to 0.5 wt. % Ca; a content of one or more other elements; and a remainder content being Mg; wherein the nanosized precipitates are less noble or more noble than the Mg matrix, or a mixture thereof. In another embodiment, the MgZnCa alloy composition consists of a Mg matrix; and, optionally, nanosized precipitates; wherein the composition has a Zn content ranging from 0.1 wt. % Zn to 2.0 wt. % Zn; a Ca content ranging from 0.2 wt. % Ca to 0.5 wt. % Ca; a content of one or more other elements; and a remainder content being Mg; wherein the nanosized precipitates are less noble or more noble than the Mg matrix, or a mixture thereof.

The terms "composition," "alloy composition," "MgZnCa alloy," and "alloy" are used interchangeably herein. Unless otherwise stated or indicated, the amounts disclosed herein are based on the weight of the alloy composition.

As used herein, the term "Mg matrix" refers to the bulk Mg portion of the alloy composition in which the constituent parts of the alloy, e.g., Zn, Ca, and/or impurities (referred to herein also as "other elements") are dissolved. For example, the Mg matrix may comprise pure Mg or Mg in solid solution with Zn, Ca, and/or impurities, or mixtures thereof. The Mg matrix would not include secondary phases, i.e., undissolved components, including precipitates.

The Mg matrix is also referred to as the Mg remainder, remainder Mg, or the surrounding Mg phase. For example, for certain embodiments, the composition may be described as a MgZnCa alloy containing nanosized precipitates, having a Zn content ranging from 0.1 wt. % Zn to 2.0 wt. % Zn and a calcium content ranging from 0.2 wt. % to 0.5 wt. %, less than 0.04 wt. % of one or more other elements, the other elements optionally located in a secondary phase, and with the remainder of the alloy being Mg, wherein the nanosized precipitates are less noble than the remainder Mg.

In some aspects of the present invention, the composition may be substantially free of microgalvanic elements. In other embodiments, the composition may be free of secondary phases, including precipitates. A composition free of secondary phases can be achieved when all components of the composition are dissolved, thus forming a monophasic composition.

In other aspects of the invention, the composition comprises a plurality of nanosized precipitates, wherein the precipitates are less noble than the Mg matrix. In some such embodiments, the nanosized precipitates that are less noble than the Mg matrix comprise $(Mg,Zn)_2Ca$. In other embodiments, the composition comprises a plurality of nanosized precipitates that are more noble than the Mg matrix. In some such embodiments, the nanosized precipitates that are more noble than the Mg matrix comprise $Mg_6Zn_3Ca_2$. The nanosized precipitates are typically less than 1000 nanometers and more typically less than 500 nanometers. In some embodiments, the nanosized precipitates range from about 1000 nanometers to about 100 nanometers, from about 500 nanometers to about 100 nanometers, or from about 300 nanometers to about 200 nanometers.

With respect to implants of the present invention, the implant has a three-dimensional structure and comprises an MgZnCa alloy disclosed herein. For example, in an embodiment, the implant has a three-dimensional structure made from a MgZnCa alloy comprising a Mg matrix and a plurality of nanosized precipitates, wherein the alloy has a Zn content ranging from 0.1 wt. % Zn to 2 wt. % Zn, a calcium content ranging from 0.2 wt. % to 0.5 wt. %, has less than 0.10 wt. % of one or more other elements, with the remainder being Mg, wherein the plurality of nanosized precipitates are less noble than the Mg matrix. In another embodiment, the implant has a three-dimensional structure and comprises a composition consisting essentially of a MgZnCa alloy comprising a Mg matrix and a plurality of nanosized precipitates, wherein the alloy has a Zn content ranging from 0.1 wt. % Zn to 2 wt. % Zn, a calcium content ranging from 0.2 wt. % to 0.5 wt. %, having less than 0.10 wt. % of one or more other elements, with the remainder being Mg and wherein the plurality of nanosized precipitates are less noble than the Mg matrix. In another embodiment, the implant has a three-dimensional structure and comprises a composition consisting of a MgZnCa alloy comprising a Mg matrix and a plurality of nanosized precipitates, wherein the alloy has a Zn content ranging from 0.1 wt. % Zn to 2.0 wt. % Zn, a calcium content ranging from 0.2 wt. % to 0.5 wt. %, has less than 0.10 wt. % of one or more other elements, with the remainder being Mg, wherein the plurality of nanosized precipitates are less noble than the Mg matrix. In such embodiments, the less noble nanosized precipitates comprise $(Mg,Zn)_2Ca$.

Generally, the Zn content in the various embodiments of the MgZnCa alloy and an implant based on the various embodiments of the MgZnCa alloy, according to the present invention, can be any suitable amount between 0.1 wt. % to 2 wt. %. In an embodiment, the MgZnCa alloy has Zn content which may be independently selected from ranges from 0.1 wt. % to 2 wt. %; 0.5 wt. % to 2 wt. %; 0.6 wt. % to 0.8 wt. %; 1 wt. % to 2 wt. %; 0.1 wt. % to 0.5 wt. %; 0.1 wt. % to 1 wt. %; and any subset of ranges set forth herein.

Generally, the Ca content in the various embodiments of the MgZnCa alloy and in an implant based on the various embodiments of the MgZnCa alloy, according to the present invention, can be any suitable amount between 0.2 wt. % to 0.5 wt. %. In an embodiment, the MgZnCa alloy has Ca content which may be independently selected from ranges from 0.2 wt. % to 0.5 wt. %; 0.2 wt. % to 0.3 wt. %; 0.2 wt. % to 0.4 wt. %; 0.3 wt. % to 0.4 wt. %, and 0.4 wt. % to 0.5 wt. %.

Generally, the alloy compositions of the present invention are based on a material free of secondary phases which otherwise act as cathodic microgalvanic cells. Often times the presence of a single impurity can decrease the solubility of the other impurities. During the solidification process, the impurities can accumulate in the interdendritic spaces of the alloy and induce the formation of secondary phases. To achieve the necessary purity level of the MgZnCa alloy embodiments described herein, the acceptable amount of other elements within the alloy is limited.

For example, the amount of total other elements within the alloy composition is typically less than 0.10 wt % based on the weight of the composition, typically less than 0.06 wt % based on the weight of the composition, and more typically less than 0.04 wt % based on the weight of the composition. The other elements may be dissolved in the Mg matrix or may be in a secondary phase, or both. Typically, the alloy comprises less than 0.04 wt % of other elements in a secondary phase.

In one embodiment, the MgZnCa alloy, having a plurality of nanosized precipitates being less noble than the Mg matrix, contains less than 400 ppm (by weight) of total other elements. In another embodiment, the MgZnCa alloy, having a plurality of nanosized precipitates being less noble than the Mg matrix, contains less than 200 ppm of total other elements. In yet another embodiment, the MgZnCa alloy, having a plurality of nanosized precipitates being less noble than the Mg matrix, contains less than 100 ppm of total other elements. In still yet another embodiment, the MgZnCa alloy, having a plurality of nanosized precipitates being less noble than the Mg matrix, contains less than 50 ppm of total other elements.

In such embodiments, the other elements can include one or more of Fe, Cu, Ni, Co, Si, Mn, Al, Zr and P.

The impurity level is maintained at low levels to control the corrosion rate once an implant, based on such alloys, is placed in the body. It is necessary to control the corrosion rate so that the implant possesses sufficient strength over a period of time to allow healing and so not to interfere with the healing process. Although the degradation by-products from the magnesium alloys of the present invention are non-toxic, as the metal corrodes the pH near the implant increases to a basic pH. Likewise, hydrogen gas produced during the corrosion process must be eliminated. In the case of endovascular implants, these concerns are insignificant as the constant blood flow over the implant removes the hydrogen gas and other degradation by-products.

Generally, the rare earth content in the various embodiments of the MgZnCa alloys compositions used in an implant, according to the present invention is limited. In such embodiments, the rare earth elements include Sc, Y, the Lanthanide elements, atomic numbers ranging from 57-71 and the Actinide elements, atomic numbers ranging from 89-103. In one embodiment, the rare earth content is less than 10 ppm. In another embodiment, the rare earth content is less than 5 ppm.

In some embodiments, the alloy is substantially free of microgalvanic elements. For the purposes of this application "microgalvanic element" refers to a secondary phase, including a precipitate, with a higher potential than the magnesium matrix (i.e. that are electrochemically more noble). For the purpose of this application, "substantially free" refers to the number of microgalvanic elements that is small enough not to change the overall degradation behavior of the alloy from an overall homogeneous degradation to a localized, pitted degradation.

The mechanical properties of the commercially pure magnesium are improved by solid solution hardening with high purity zinc without affecting the homogeneous nature of the alloy. A fine grained microstructure can be achieved by plastic deformation and stabilized with secondary phases, including precipitates, which are less noble than the magnesium matrix. For example, the less noble $(Mg,Zn)_2Ca$ phase can be obtained by small additions of high purity calcium and adequate heat treatment. If needed, the degradation rate can be accelerated, while maintaining a uniform corrosion profile, by modification of the composition and the aging heat treatment to form precipitates which are more noble than the magnesium matrix, such as fine $Mg_6Zn_3Ca_2$ precipitates.

Also disclosed are implants, such as implantable medical devices, made from the compositions disclosed herein. The disclosed implants have advantageous physical properties, including high yield strength, high ultimate tensile strength, and elongation at break. In some embodiments, the alloy has the yield strength of at least 180 MPa. In some embodiments, the alloy has the yield strength of at least 200 MPa. In other embodiments, the alloy has a yield strength of at least at least 220 MPa. In some embodiments, the alloy has an ultimate tensile strength of at least 240 MPa. In other embodiments, the alloy has an ultimate tensile strength of at least 260 MPa, at least 280 MPa, at least 300 MPa, at least 320 MPa, at least 340 MPa, at least 360 MPa, or at least 380 MPa. In some embodiments, the alloy has at least 10% elongation at break. In other embodiments, the alloy has elongation at break values of: at least 12%, at least 14%, at least 16%, at least 18%, at least 20%, and at least 22%.

Implants according to exemplary embodiments of the present invention also have advantageous chemical properties in vitro and in vivo. In some embodiments, the alloy has an in vitro degradation rate of less than 1.0 $mg/cm^2/day$. In other embodiments the alloy has an in vitro degradation rate of less than 0.5 $mg/cm^2/day$ as measured in a simulated body fluid. In other embodiments, the alloy has an in vitro degradation rate of less than 0.05 $mg/cm^2/day$, less than 0.1 $mg/cm^2/day$, less than 0.15 $mg/cm^2/day$, less than 0.2 $mg/cm^2/day$, less than 0.25 $mg/cm^2/day$, less than 0.3 $mg/cm^2/day$, less than 0.35 $mg/cm^2/day$, less than 0.4 $mg/cm^2/day$, or less than 0.45 $mg/cm^2/day$, as measured in a simulated body fluid.

Implantable medical devices based on the compositions described herein can be manufactured for a variety of medical/clinical applications, including replacing a missing biological structure, to support a damaged biological structure, or to enhance an existing biological structure. The composition of the implants and/or the surfaces of the implants that contact the body/body tissues can be varied depending on the particular application under consideration. Surgical implants can be manufactured for medical/clinical applications in the area of orthopedics, neurosurgery, among others. Non-limiting examples of surgical implants include: neurosurgical implants, e.g. hydrocephalus shunts and components; intracranial aneurysm clips; bone and joint replacements, e.g., partial and total hip joint prostheses and total knee-joint prostheses; osteosynthesis and spinal devices, e.g., metal bone screws, metal bone plates, medullary pins, metallic skeletal pins and wires, and total intervertebral spinal disc prostheses; oral and maxillo facial surgery implants; and spinal and pelvic systems such as Universal Spine System, Harrington System, and conventional systems. Accordingly, surgical implants that can be manufactured based on the compositions described herein can include a wide range of products varying in composition as described herein, structural complexity and medical/clinical applications. As such, implants for use in accordance with exemplary embodiments of the present invention can vary in size, shape, and other physical and chemical characteristics depending upon the context of use.

In some embodiments, the implant is an orthopedic implant. In such embodiments, the orthopedic implant comprises one or more of the following: a nail, a screw, a staple, a plate, a rod, a tack, a bolt, a bolt to lock an IM nail, an anchor, a dowel, a plug, a peg, a sleeve, a mesh, a transconnector, a nut, a shaped body, spinal cage, a wire, a K-wire, a woven structure, clamp, splint, scaffold, foam and honeycomb structure. In some other embodiments, the implant has a lower degradation rate compared to magnesium alloy implants containing microgalvanic elements.

In other embodiments, the implant is a non-orthopedic implant. In such embodiments, the non-orthopedic implant includes a cardiovascular stent, a neuro stent and a vertebroplasty stent.

In vitro degradation tests in simulated body fluid (SBF) with Tris buffer show that a uniform degradation with extremely low degradation rate can be achieved when using the MgZnCa alloys of the present disclosure (see, e.g., FIG. 3C). These alloys, however, would have poor mechanical properties in comparison to alloys like WE43 if no particular measures are taken. This limitation, it has been discovered, can be overcome by strict control of the grain size during all processing steps including casting. The hardening of the alloy can be achieved by refining the grain microstructure using plastic deformation (extrusion, forging, equal channel angular compression, etc.). In addition to achieving a better strength level, the fine grained microstructure was also found to avoid mechanical anisotropy (strength difference between tension and compression).

The present disclosure further provides for methods of making various embodiments of the MgZnCa alloy described herein. In one embodiment, the method includes the steps of: (a) casting an alloy containing (i) commercially pure magnesium having a purity of at least 99.96 wt. %; and (ii) from 0.1 to 2.0 wt. % zinc having a purity of at least 99.9 wt. % and (iii) from 0.2 to 0.5 wt % calcium having a purity of a least 99.9 wt %, said casting preferably being performed in an inert atmosphere and an inert reaction vessel; (b) solution heat treating the cast alloy at two different temperatures wherein a first temperature is below an eutectic temperature of Mg—Zn and a second temperature is above the eutectic temperature of the ternary Mg—Zn—Ca system to thereby form a MgZnCa alloy containing from 0.1 wt. % Zn to 2 wt. % Zn and 0.2 wt % Ca to 0.5 wt % Ca (c) aging heat treatment between 100° C. and 300° C.; and (d) extruding the alloy into a desired shape. In some embodiments, the MgZnCa alloy is monophasic. In some embodiments, the method may further include the step of a second aging heat treatment of the shaped alloy to improve either strength or ductility of the alloy. In other embodiments, the method includes a low temperature heat treatment of the shaped alloy, e.g., from about 150° C. to about 250° C., to adjust the degradation profile of the alloy. As used above, the eutectic temperature of Mg—Zn refers to a pseudobinary Mg—Zn system with 0.2 to 0.5 wt % Ca, wherein pseudobinary is the cut through the ternary phase diagram for a given calcium content.

The impurity limits for the magnesium are preferably: Fe<30 ppm, Cu<20 ppm, Ni<5 ppm, Mn<200 ppm, Si<200 ppm whereas the total amount of these impurities should preferably be below 400 ppm. In certain embodiments, $(Mg,Zn)_2Ca$ precipitates are formed and are one of the few phases which are electrochemically less noble than pure magnesium.

In certain embodiments, the first temperature is in a range from about 200° C. to about 400° C., from about 300° C. to about 400° C., or from about 330° C. to about 370° C. Typically the cast alloy is heated at the first temperature from about 6 to about 24 hours. The second temperature is typically in the range of about 400° C. to about 600° C., from about 400° C. to about 500° C., or from about 400° C. to about 460° C. The second temperature is preferably above the solvus temperature of any potential precipitates in order to make sure all elements of the alloy are in solid solution. Typically, the cast alloy is heated at the second temperature from about 4 hours to about 16 hours. The aging heat treatment is typically between 100° C. and 300° C., and, in certain, embodiments between about 150° C. and about 250° C. Typically, the aging heat treatment is done for about 0.5 hours to about 6 hours. Such aging treatment creates fine and homogenously distributed nanosized precipitates prior to the extrusion process.

Figure 4A:
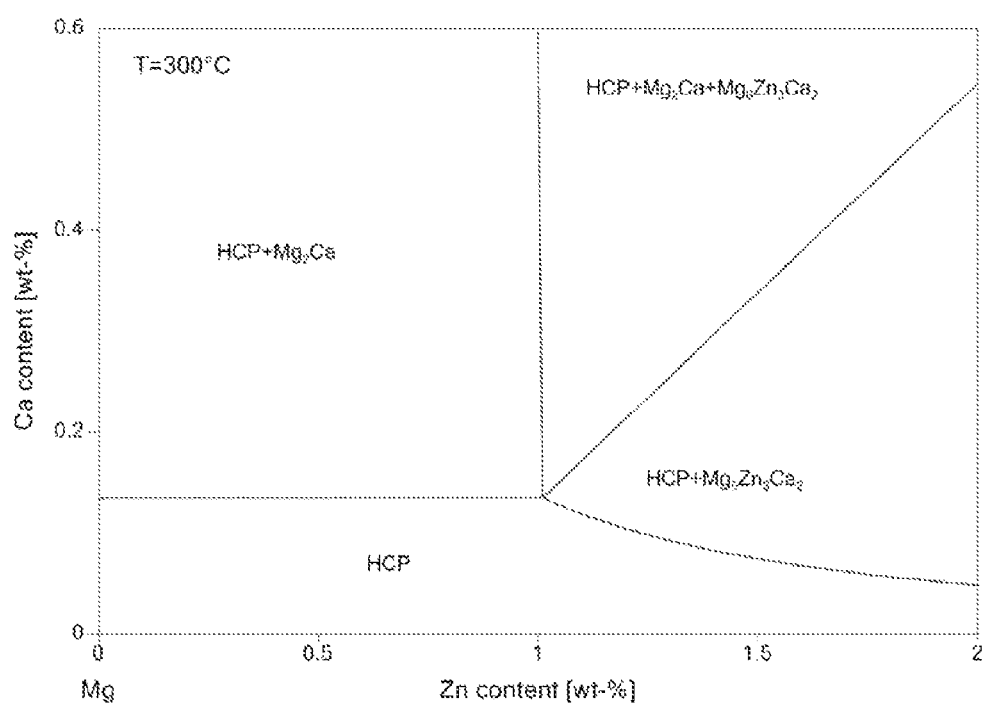
FIGS. 4A-4B, are a (A) graphical representation of an isothermal section of an Mg—Zn—Ca system at 300° C. and (B) illustration of the constitution of an MgZn1Ca0.3 alloy according to the present disclosure.
Figure 4B:
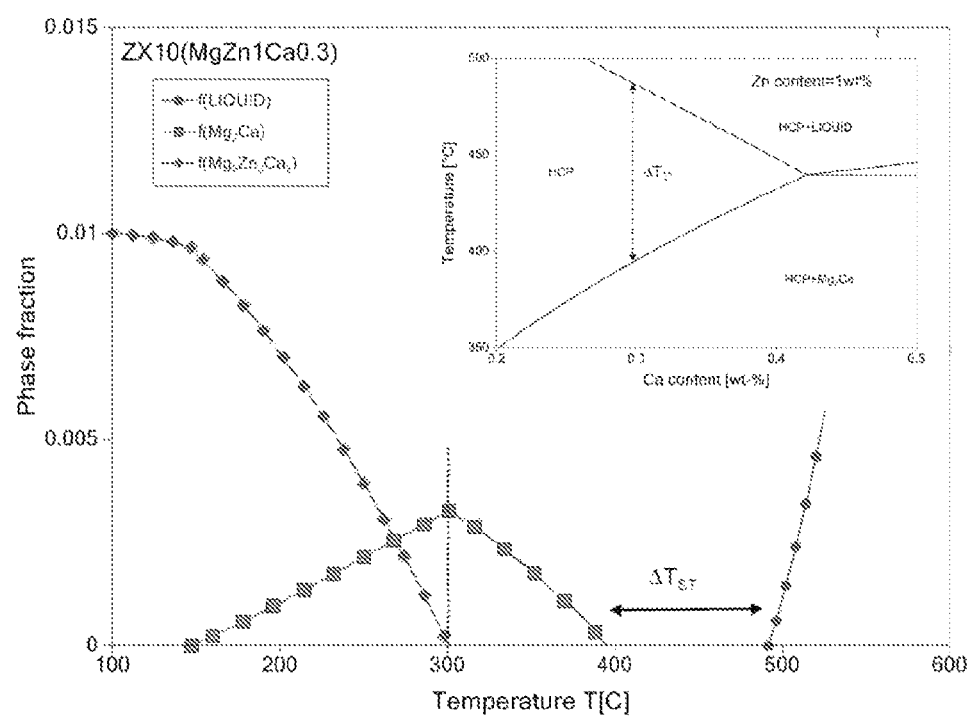

Phase calculations of the MgZnCa alloy system have shown that a compositional window exists for low Zn and Ca contents where complete dissolution of the alloying elements is possible and no second phase, from the casting process, remains after a solution heat treatment (see, e.g., FIG. 4B). While not wishing to be bound by theory, it was believed that advantageous properties could result from a stable fine grained microstructure within the alloy and that such a microstructure could be obtained if the grain boundaries are pinned by the presence of fine precipitates. It was found that an aging heat treatment, prior to extrusion, results in the formation of nanosized precipitates which are not visible under an optical microscope but which are large enough to prevent the grains from coarsening due to static recrystallization. These precipitates do not influence the dynamic recrystallization behavior during the extrusion process. Grain refinement, therefore, remains possible whereas coarsening is prevented or at least retarded. Furthermore, as the precipitates are less noble than the magnesium matrix and have no 3-dimensional connectivity among themselves, the precipitates do not deteriorate the degradation performance of the alloy. Without wishing to be bound by theory, it is believed that the magnesium matrix has no 3-dimensional connectivity because the precipitates are not formed during solidification, but rather after complete dissolution of the elements and subsequent heat treatment. The MgZnCa alloy system, having the less noble fine precipitates, exhibits fine grain sizes less than 5 μm after extrusion of the casting billet, including less than 2 μm, and less than 1 μm.

For example, with the addition of 0.1 wt. % to 2.0 wt. % Zn and 0.2 wt. % to 0.5 wt. % Ca to Mg, such finely dispersed precipitates can be created by an aging heat treatment following the initial solution heat treatment. The weight percentage of calcium and zinc can be adjusted to control the degradation rate of the alloy. If the degradation rate of the alloy is too slow and needs to be accelerated, $Mg_6Zn_3Ca_2$ precipitates can be formed by slightly changing the alloy composition. As an example, for a Mg alloy with 1 wt. % Zn and 0.35 wt. % Ca, mainly $(Mg,Zn)_2Ca$ nanoparticles are precipitated by an aging heat treatment at 200° C. whereas for a Mg alloy with 1.5 wt. % Zn and 0.25 wt. % Ca, mainly $Mg_6Zn_3Ca_2$ nanoparticles precipitate at the same temperature.

In an alternative embodiment, the aging heat treatment step may be replaced with a heat treatment performed during the extrusion step, e.g., during preheating and extrusion. Preheating for extrusion is typically carried out at the extrusion temperature in a separate oven until the billet has reached a uniform temperature. The preheated billet is then transferred to the preheated extrusion chamber and extrusion is carried out. If precipitates form during this preheating step, it would be considered an aging treatment.

After the alloy is shaped, a low temperature heat treatment, such as an annealing step, can be performed. In some embodiments, a low temperature annealing step is performed after the extrusion step.

For example, low temperature annealing is a heat treatment, typically of the shaped alloy, at a temperature and time sufficient to affect precipitate formation, and, as a result, degradation properties. In particular, it has been found that low temperature annealing can lead to the growth of more noble precipitates, such as $Mg_6Zn_3Ca_2$ precipitates, that accelerate the overall degradation of the alloy. In addition, a low temperature annealing process also can affect the microstructure of the alloy, with a longer annealing process leading to increased grain size.

In some embodiments, the low temperature annealing is performed in a range from about 100° C. to about 300° C., or from about 150° C. to about 250° C. For example, in some embodiments, the low temperature annealing is performed at 200° C. Typically the low temperature annealing is performed from about 1 to about 100 hours.

The magnesium alloys in the exemplary embodiments described above have especially favorable properties for processing and for their later intended purpose in comparison with traditional magnesium alloys: the ductility of the magnesium alloys is greatly elevated. For purposes of the present disclosure, the term "ductility" (or toughness, deformation capacity) refers to the ability of a metallic material to undergo permanent deformation under sufficiently high mechanical loads before cracking occurs. This ability is of great importance for many construction parts because only a ductile material is capable of dissipating local mechanical stress peaks by undergoing permanent deformation without cracking and with simultaneous cold solidification. This aspect, in particular, makes it especially advantageous to use the inventive magnesium alloys as a material, for example, for biodegradable implants, in particular, biodegradable bone fixation implants. With a given material, the ductility depends on the temperature, the stress rate, the multi-axle character of the acting mechanical stress state and the environment. Characteristic values of ductility include, e.g., the elongation at break and necking, the notched impact strength and the fracture toughness as described elsewhere herein.

EXAMPLES

For purposes of further disclosure, certain high Zn-containing alloys (MgZn5Ca0.25), referred to as ZX50, were prepared along with lower Zn alloys as disclosed herein, such as MgZn1Ca0.3, referred to as ZX10. The alloys were also prepared with varying degrees of purity: "Conventional purity" (CP), "high purity" (HP), and "vacuum-distilled ultra-high purity" (XHP). Reference regarding purity level designations may also be made to ASTM standard B92/B92M-11. For the particular CP ZX50 sample described herein, a Mg ingot with 99.8 wt % purity was used. The purity of the HP and XHP samples are noted below.

Preparation of Mg Alloys

For the production of HP ZX50, high-pure Mg (99.98%), Ca (99.0%), and Zn (99.99%) was used. For the XHP alloys ZX50 and ZX10, distilled ultra-pure Mg (99.999%), Ca (99.99%), and Zn (99.999%) were synthesized in a graphite crucible under a protective gas mixture at 750° C. Subsequently, the melt was poured into a conical graphite mold (average diameter 55 mm, height≈150 mm) which was water-cooled at the bottom to force directional solidification in order to avoid shrinkage cavities. Afterwards the billets were homogenized, i.e., solution treated (ZX50 alloys: 350° C./12 h; ZX10 alloy: 350° C./12 h plus 450° C./8 h) followed by cooling with pressurized air. The chemical compositions of certain of the samples were determined by glow discharge mass spectrometry (shown in Table 1).

Extrusion Procedure

The homogenized alloys were machined to billets with 50 mm in diameter and 120 mm in length. For XHP ZX10, the billet was aged at 250° C. for 30 min in order to create fine and homogeneously distributed intermetallic particles (precipitates) prior to the extrusion process. Afterwards the billet was heated to 300° C. and indirect extrusion was performed at a ram speed of 0.15 mm/s to a rod profile with a diameter of 10 mm, corresponding to an extrusion ratio of 25:1. Cooling with pressurized air was applied at the exit side of the extrusion press. For the ZX50 alloys the extrusion to 10 mm diameter was performed by direct extrusion at 325° C. It has been found that indirect extrusion leads to higher rates of dynamic recrystallization.

In order to check the influence of trace elements on degradation performance, ZX50 alloys were prepared using high-purity (HP) Mg and vacuum-distilled ultra-high purity (XHP) Mg (see WO2013/107644 regarding vacuum distillation of high purity Mg, incorporated herein by reference). The chemical composition, including reference to "harmful" elements, is given in Table 1. The use of XHP-Mg and ultrapure Zn and Ca for the XHP ZX50 synthesis results in a reduction of the trace element content by a factor of about 100.

TABLE 1

Chemical composition of ZX50 with conventional purity (CP), high-purity (HP), and ultra-high purity (XHP).

| Alloy | Zn [wt-%] | Ca [wt-%] | Mn [ppm] | Si [ppm] | Fe [ppm] | Cu [ppm] | Ni [ppm] | Co [ppm] |
|---|---|---|---|---|---|---|---|---|
| CP ZX50 | 5.24 | 0.27 | 1630 | 440 | 42 | 9 | 8 | 8 |
| HP ZX50 | 5.21 | 0.29 | 160 | 430 | 31 | 8 | 7 | 5 |
| XHP ZX50 | 5.26 | 0.31 | 0.8 | 2.9 | 0.5 | 0.09 | 0.05 | <0.05 |

Immersion Tests

The degradation of the alloys was measured by the hydrogen evolution method as described in G. Song, A. Atrens. D. H. St John, Magnesium Technology Conference at TMS. New Orleans, La., USA, (2001) 255 (herein incorporated by reference) and evaluated using an in-house improved testing setup as described in M. Schinhammer, J. Hofstetter, C. Wegmann, F. Moszner, J. F. Löffler, P. J. Uggowitzer, "On the immersion testing of degradable implant materials in simulated body fluid: Active pH regulation using $CO_2$" Adv. Eng. Mater. 15 (2013) 434-441 (herein incorporated by reference). The device exhibits a high gas volume resolution and was especially designed for slow degrading materials; it accounts also for the daily atmospheric pressure fluctuations and gas dissolution. The specimen sizes were used with surface areas in the range of $259\pm1$ mm$^2$ to $626\pm6.7$ mm$^2$. Three specimens per batch were tested and their mean hydrogen evolution was evaluated to ml/cm$^2$. All data points were corrected by the atmospheric pressure and the gas dissolution. The ion concentration of the SBF used for the immersion tests is described in A. C. Hänzi, I. Gerber, M. Schinhammer, J. F. Löffler, P. J. Uggowitzer, "On the in vitro and in vivo degradation performance and biological response of new biodegradable Mg—Y—Zn alloys" Acta Biomater. 6 (2010) 1824-1833 (herein incorporated by reference); either $CO_2$ (99.90 vol %) or Tris was used as buffer. During the degradation test, the pH was set at $7.45\pm0.017$ with a temperature of $36.91\pm0.30°$ C. for two weeks. The samples were ground on abrasive SiC paper of granularity 4000. Just before immersion, they were polished on a 1 µm polishing cloth, cleaned in an ultrasonic bath using isopropanol and dried in hot air.

FIG. 1, which shows the mean hydrogen evolution versus time of the conventional purity (CP), high-purity (HP), and ultra-high purity (XHP) ZX50 alloys immersed in $CO_2$-buffered simulated body fluid (SBF) with pH 7.45 at 37° C. (note the different scales at y-axis; typical data scatter is illustrated by error bars), illustrates the importance of impurity level. The amounts of hydrogen increase steadily at the beginning with a slight decrease in degradation rate with increasing time. The XHP ZX50 alloy evolves significantly less hydrogen than the CP and HP alloy within the same time. This significant improvement (after 2 weeks by more than an order of magnitude from CP to HP, and a factor of ~3 from HP to XHP) can be attributed to the reduced trace element content and the related avoidance of degradation-generating cathodic sites.

Changing from a $CO_2$-buffer to the organic compound Tris results in an increased degradation rate and is accompanied by a change in the character of the corrosion morphology. For the alloys in $CO_2$-buffered SBF, a very homogeneous degradation is observed (FIG. 3A), while in Tris-SBF a distinct localized corrosion attack is observed, and the local attack is most pronounced on the fast degrading alloys ZX50 (FIG. 3B). However, such change in the degradation morphology does not take place in unalloyed Mg. Furthermore, only very weak localized attack is notable on alloy XHP ZX10 (FIG. 3C). These findings suggest a strong influence of the alloy's chemical composition on the degradation susceptibility in specific environments.

Figure 3:
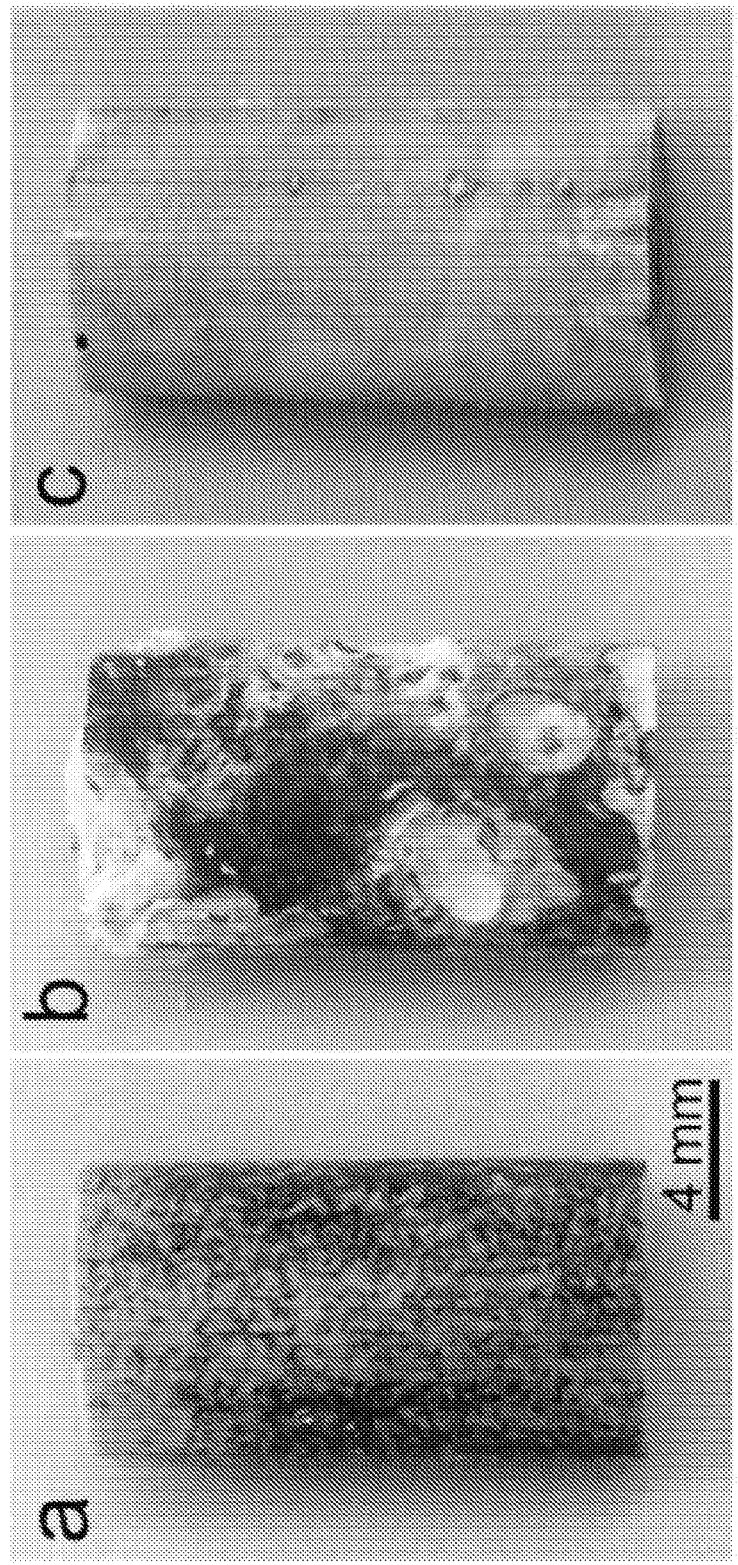
FIG. 3 depicts the surface topography of implant samples after immersion in simulated body fluid (SBF).

FIG. 3 illustrates the surface topography of samples after immersion in SBF as follows: (a) XHP ZX50 shows no local corrosion attack after two weeks immersion in CO2-buffered SBF and (b) distinct localized attack in Tris-buffered SBF after only 3 days; (c) no indication of local corrosion attack is visible for XHP ZX10 after 2 weeks immersion in Tris-buffered SBF.

FIG. 4A illustrates the constitution of Mg—Zn—Ca alloys at 300° C., i.e. the temperature used for extrusion in production of the ZX10 alloy (the hot forming temperature). As used in FIGS. 4A and B, "HCP" stands for hexagonal-closed packed, and refers to the crystal structure of the Mg matrix. In order to avoid formation of the ternary $Mg_6Zn_3Ca_2$ phase, it is seen that the Zn content should be below ~1.0 wt %, but in order to also benefit from some solid solution hardening, 1 wt % was chosen for the ZX10 alloy, and the content of Ca was evaluated along with the grain-refining effect of $Mg_2Ca$ particles. To create a very fine particle size, a solution treatment followed by an ageing procedure below or at the hot forming temperature was performed (see extrusion method above). FIG. 4B shows (a) the width of the solution treatment window $\Delta T_{ST}$ (Zn and Ca are completely dissolved in Mg and the solidus temperature is still not reached) at a Zn content of 1 wt % and (b) the influence of the Ca content on the width of the solution treatment window. In this case, 0.3 wt % Ca was chosen. The constitution of the Zn-lean alloy MgZn1Ca0.3 (ZX10) is shown in FIG. 4A. At 300° C. only the $Mg_2Ca$ phase is present. $Mg_2Ca$ and $(Mg,Zn)_2Ca$ are equivalent; $Mg_2Ca$ can contain some Zn without changing its nature. According to their Zener drag effect the resulting grain size stays at low levels, i.e. ~2 µm (see extrusion parameters above). The corresponding mechanical properties of alloy ZX10 are as follows. In tension: yield strength (TYS)=240 MPa, ultimate tensile strength (UTS)=255 MPa, elongation to fracture=27%; in compression: compression yield strength (CYS)=205 MPa, ultimate compression strength (UCS)=245 MPa, elongation to fracture=13%. The tension and compression conditions are determined by ASTM or ISO standards (e.g., compression DIN 50106 and tension DIN EN 10002-1). The ZX10 alloy features not only high strength and good ductility but also low mechanical anisotropy.

Figure 2:
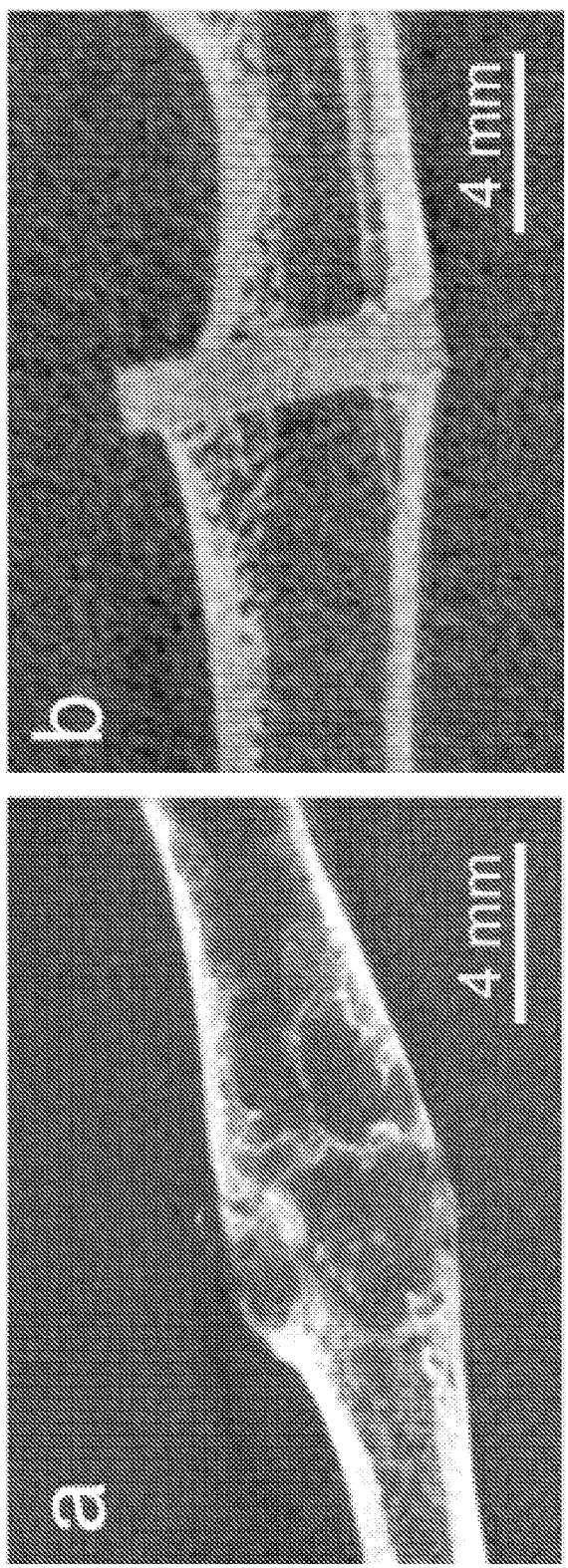
FIG. 2 depicts μCT reconstructions (2-D slices) of Mg-pins implanted into the femur of Sprague-Dawley rats 12 weeks post operation.

As shown in FIG. 2, the good mechanical properties of alloy XHP ZX10 are accompanied by excellent bio-corrosion behavior. FIG. 2 illustrates the in vivo degradation performance of alloy XHP ZX10 (FIG. 2B) compared to CP ZX50 (FIG. 2A) after 12 weeks implantation time. The fast corroding CP ZX50 has completely degraded and severe irritation of the bone is observed, while the XHP ZX10 exhibits a desired slow and homogenous degradation. In this case, no hydrogen bubbles can be clinically observed and the living organism was able to absorb the generated low amount of hydrogen, a fact that is of high relevance from a medical point of view.

Low Temperature Annealing

Figure 5:
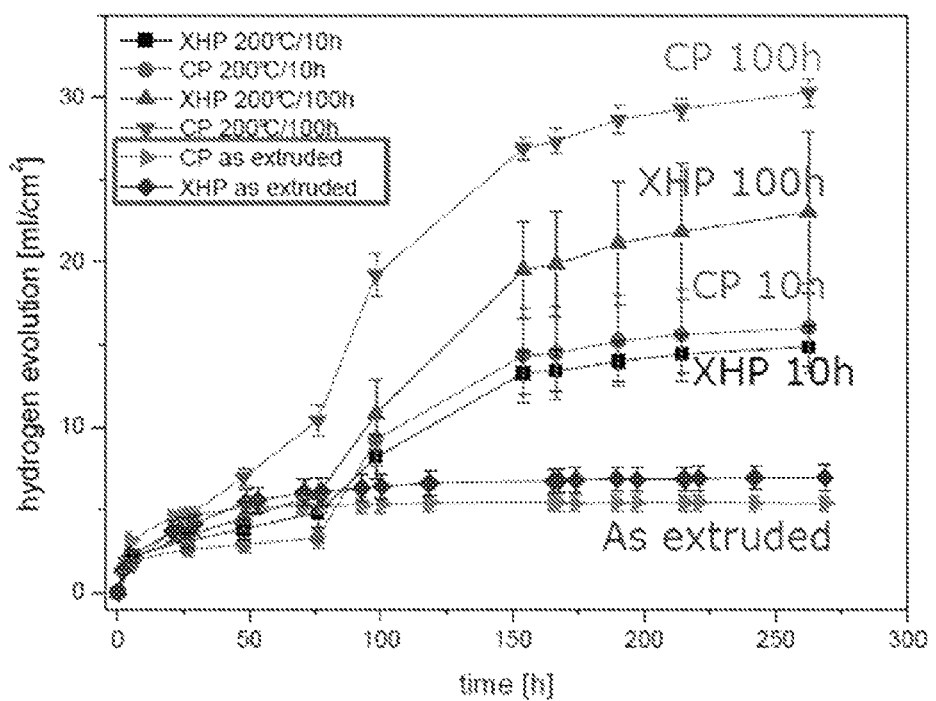
FIG. 5 is a graphical representation of mean hydrogen evolution during immersion in TRIS buffered simulated body fluid versus time of certain Mg alloys that were subjected to certain heat treatments.
Figure 6:
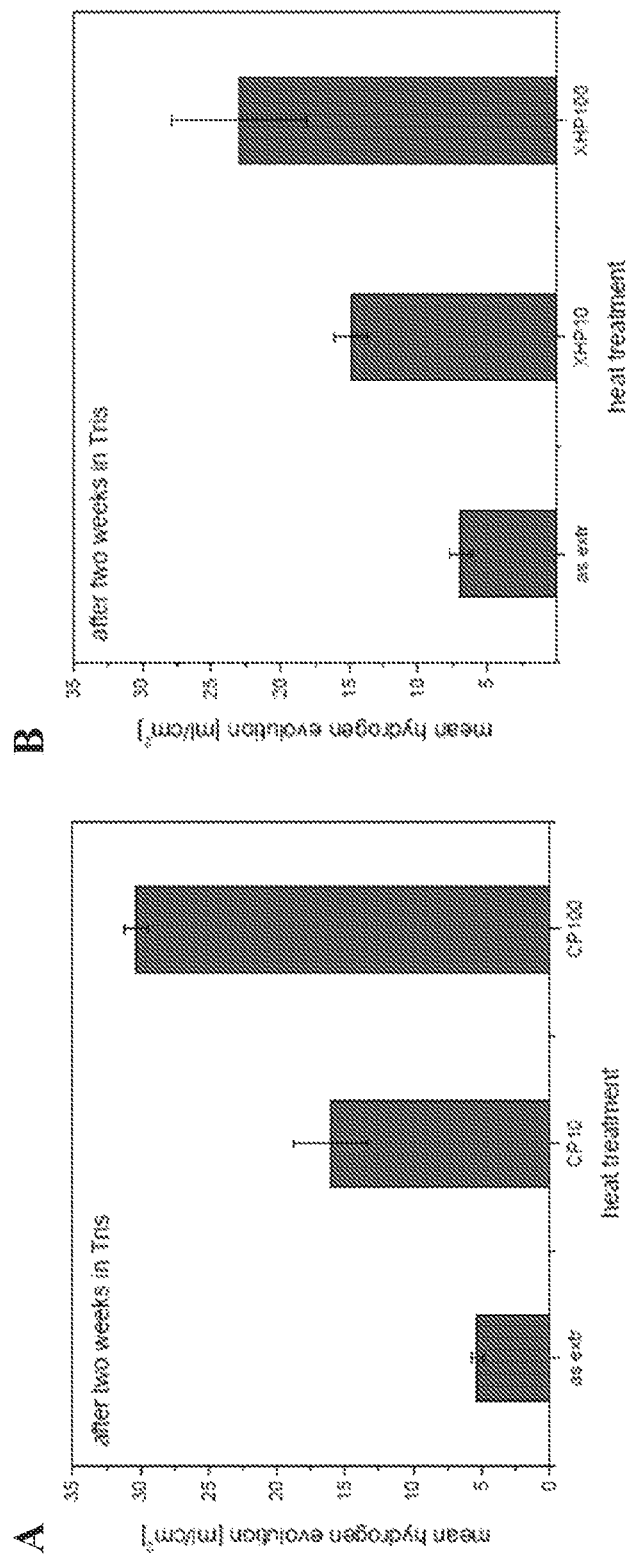
FIG. 6, comprising

CP ZX10 (having the following impurities as measured by optical emission spectroscopy (OES): Al: 229 ppm; Cu: 11 ppm; Fe: 32 ppm; Mn: 309 ppm; Ni: 10 ppm; Si: 323 ppm; and Zn: 47 ppm) and XHP ZX10 alloys were prepared as described above for ZX10 alloys (i.e. MgZn1Ca0.3). After the extrusion procedure, CP ZX10 and XHP ZX10 alloys were subjected to a low temperature annealing at 200° C. for 10 hours (h) and 100 hours (h) and immersion tests were performed, as described above, in Tris-buffered SBF. As shown in FIG. 5, the degradation rate of the alloys increases as the time of the low temperature annealing step increases. For example, alloys subjected to a low temperature annealing for 100 h degrade at a faster rate than those subjected to a low temperature annealing for 10 h. Furthermore, alloys that are subjected to a low temperature annealing exhibit an increased degradation rate compared to alloys that do not undergo a low temperature annealing step (compare "as extruded" with 10 h and 100 h). Additionally, FIG. 5 shows that CP alloys degrade at a faster rate compared to XHP alloys as a result of the low temperature annealing step. The results of the low temperature annealing are further exemplified in FIGS. 6A and 6B, which show that alloys subjected to a 100 h low temperature annealing degrade faster than alloys subjected to a 10 h low temperature annealing after two weeks in Tris-buffered SBF, and both of these degrade faster than alloys not subjected to low temperature annealing (as extruded <10 h<100 h).

Figure 7:
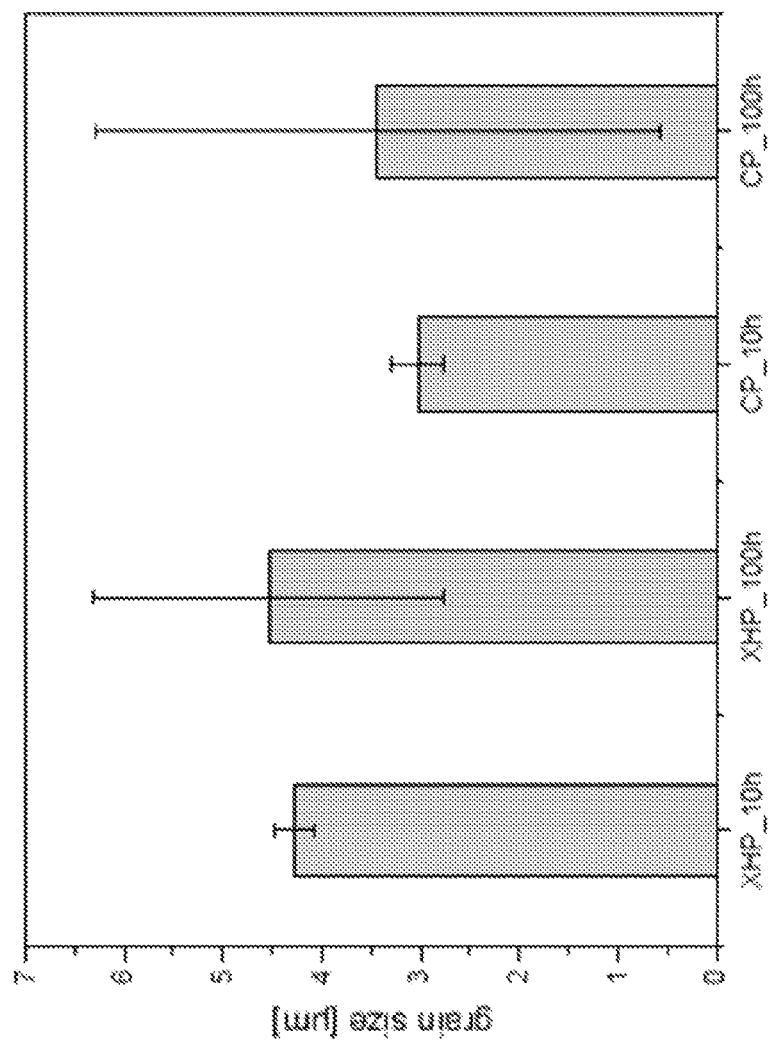
FIG. 7 is a bar graph depicting grain size for certain extruded Mg alloys that were subjected to certain heat treatments.

As shown in FIG. 7, low temperature annealing increases the grain size of the CP ZX10 and XHP ZX10 alloys. For example, the as extruded CP ZX10 alloys exhibit a grain size of about 2 µm (data not shown), a grain size of about 3.0 µm following low temperature annealing for 10 h, and a grain size of about 3.4 µm following low temperature annealing for 100 h. Similarly, the as extruded XHP ZX10 alloys exhibit a grain size of about 2 µm (data not shown), a grain size of about 4.3 µm following low temperature annealing for 10 h, and a grain size of about 4.5 µm following low temperature annealing for 100 h. Thus, in terms of grain size, as extruded <10 h<100 h. Furthermore, following low temperature annealing, the grain size of the XHP ZX10 alloys is larger than the grain size of the CP ZX10 alloys. Error bars represent standard deviation in FIGS. 5, 6, and 7.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

We claim:

1. A method of producing a composition comprising a Mg matrix and nanosized precipitates; wherein the composition has a Zn content ranging from 0.1 wt. % Zn to 2.0 wt. % Zn; a Ca content ranging from 0.2 wt. % Ca to 0.5 wt. % Ca; a content of one or more other elements; and a remainder content being Mg; wherein the nanosized precipitates are less noble or more noble than the Mg matrix, or a mixture thereof, the method comprising the steps of:
    (a) casting a mixture containing (i) magnesium having a purity of at least 99.96 wt. %; (ii) from 0.1 wt. % to 2.0 wt. % zinc having a purity of at least 99.9 wt. %; and (iii) from 0.2 wt. % to 0.5 wt. % calcium metal having a purity of at least 99.9 wt. %;
    (b) solution heat treating of the cast alloy at two different temperatures wherein a first temperature is below an eutectic temperature of Mg—Zn and a second temperature is above the eutectic temperature of the ternary Mg—Zn—Ca system to thereby form a MgZnCa alloy containing from 0.1 wt. % Zn to 2 wt. % Zn, and a calcium content ranging from 0.2 wt. % to 0.5 wt. %, and having a content of one or more other elements, with the remainder being Mg,
    (c) age heat treating between 100° C. and 300° C. to create dispersed nanosized precipitates prior to extrusion;
    (d) extruding the alloy into a desired shape; and
    (e) low temperature annealing of the shaped alloy at about 150° C. to about 250° C.

2. The method of claim 1, wherein the first temperature is from about 330° C. to about 370° C.

3. The method of claim 1, wherein the second temperature is from about 400° C. to about 460° C.

4. The method of claim 1, wherein the content of the one or more other elements is less than about 0.1 wt % of the composition.

5. The method of claim 1, wherein at least some of the one or more other elements are located in a secondary phase.

6. The method of claim 5, wherein the one or more other elements located in the secondary phase are less than 0.04 wt % of the composition.

7. The method of claim 1, wherein the alloy composition contains less than 400 ppm of total other elements.

8. The method of claim 1, wherein the one or more other elements comprise Fe, Cu, Ni, Co, Si, Mn, Al, Zr or P.

9. The method of claim 1, wherein the low temperature annealing is performed at 200° C.

10. The method of claim 1, wherein the low temperature annealing is performed from about 1 hour to about 100 hours.

* * * * *